United States Patent [19]
Karickhoff

[11] Patent Number: 4,491,398
[45] Date of Patent: Jan. 1, 1985

[54] HAND-HELD KERATOMETER

[75] Inventor: John R. Karickhoff, Fairfax, Va.

[73] Assignee: Surgidev Corporation, Minneapolis, Minn.

[21] Appl. No.: 326,041

[22] Filed: Nov. 30, 1981

[51] Int. Cl.³ .............................................. A61B 3/10
[52] U.S. Cl. .................................... 351/211; 351/212
[58] Field of Search ............... 351/211, 212, 237, 241, 351/218

[56] References Cited
U.S. PATENT DOCUMENTS 1,944,406  1/1934  Crofton ................................ 351/211
4,256,385  3/1981  Cohen et al. ......................... 351/212
4,426,141  1/1984  Holcomb ............................. 351/212

Primary Examiner—Jon W. Henry
Assistant Examiner—P. M. Dzierzynski
Attorney, Agent, or Firm—Epstein & Edell

[57] ABSTRACT

A hand-held keratometer is formed of a handle mounting a circular ring of transparent material having a roughened surface to collect incident light and project a circle of light for use in measuring roundness and, therefore, astigmatism of an eye while being held in the hand of a surgeon, the keratometer carrying indicia to permit the surgeon to radially locate the axis of astigmatism and determine the extent of astigmatism.

3 Claims, 5 Drawing Figures

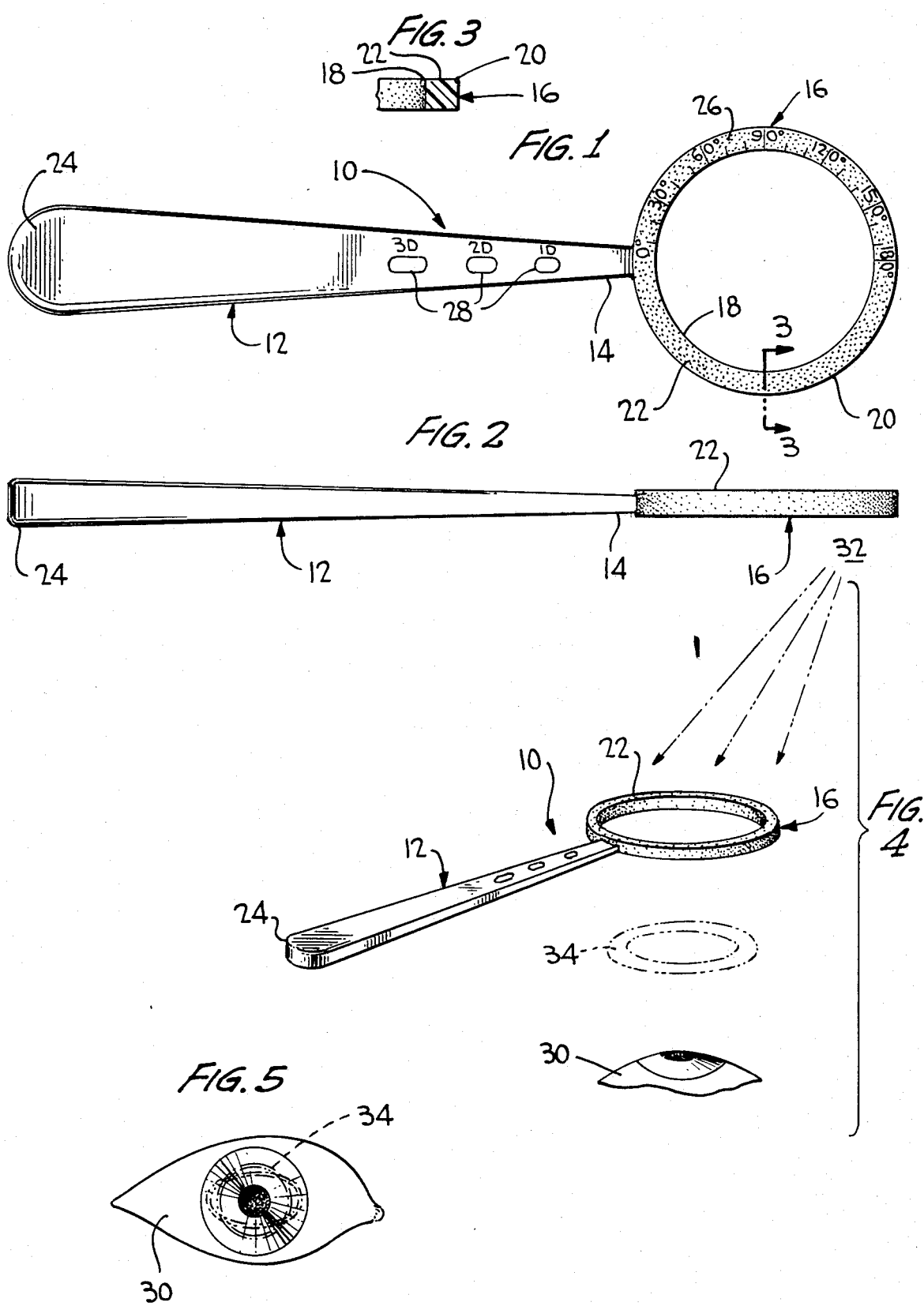

HAND-HELD KERATOMETER

BACKGROUND OF THE INVENTION

1. Field of the Invention

The present invention pertains to keratometers for measuring the roundness of the cornea of an eye and, more particularly, to a hand-held keratometer for projecting a circle of light on the cornea to measure roundness thereof.

2. Discussion of the Prior Art

After ocular surgery, it is important that the cornea remain round to avoid astigmatism in that, if the cornea is round, no correction for astigmatism need be incorporated in glasses for the patient thereby reducing the thickness and distortion of the glasses as well as the expense thereof. The problem of leaving the eye non-astigmatic has been increased with the acceptance and increased frequency of intraocular lens implant surgery in that, by eliminating astigmatism and choosing the proper power implant, a patient having intraocular lens implants will not require glasses for distant or near vision, whichever is chosen. There are only two structures in an eye having an intraocular lens implant therein that can cause astigmatism, one structure being the intraocular lens, which is manufactured to be non-astigmatic, and the other structure being the cornea, which can be manipulated to be non-astigmatic. Accordingly, astigmatism commonly associated with the natural lens in an eye is not a problem in an eye having an intraocular lens implant. Thus, the wide acceptance of intraocular lens implant surgery has greatly increased the interest in and importance of controlling the shape of the cornea as surgery is concluded since the cornea is the only source of astigmatism remaining in the eye. With astigmatism controlled, cataract surgery with insertion of an intraocular lens implant of proper power in place of the natural lens can result in clear vision without glasses whereas, without astigmatism control, such surgery can be expected to usually produce only clear vision with glasses.

To recognize astigmatism of the eye, usually a circle of light is held above the eye, and the observer looks at the reflection of the circle of light on the cornea. If the reflected light is a perfect circle, the eye is round and non-astigmatic. If, however, the reflected light is an oval, the cornea is not round and is astigmatic. The shape of the oval and the positioning of the axis of the oval is indicative of the amount and axis of the astigmatism.

Astigmatisms are usually corrected by tightening or loosening one or more of the sutures that close the cornea-scleral wound made for removal of the cataract. It has been found that tightening a suture flattens the peripheral cornea and steepens the central cornea in the visual axis. For example, if the reflection from the cornea of the circle of light was an oval with its longest dimension or axis in the vertical direction, this would indicate the cornea was flattened in the 12-6 o'clock axis. The 12 o'clock suture would then be tightened to make the cornea round. Pieces of cornea tissue can be removed, sutures loosened, and radial incisions can also be made to correct cornea astigmatism.

Prior art devices for forming a circle of light to be projected on the cornea for detecting astigmatism include surgical keratometers designed to rest on the eye in ocular contact, keratometers permanently mounted on operating microscopes and using fiber optics to produce spots of light arranged in a circle with a grid for evaluating roundness, and keratometers permanently mounted on operating microscopes wherein the reflection of the circle of light from the cornea is evaluated with prism images and a microcomputer provides a digital readout of the amount and axis of astigmatism. Such prior art keratometers suffer the disadvantages of requiring contact with the eye, of being extremely expensive and/or of being of a complex design and difficult to manipulate and operate.

Another proposed device is formed of a clear glass ring held by a stainless steel rim with a stainless steel handle to provide a hand-held, non-ocular contact keratometer. This device suffers the disadvantages of being relatively expensive to produce due to the separate manufacture of the glass ring and the stainless steel rim requiring mounting together, of the glass ring being fragile and breakable if dropped, and of requiring a light source to be disposed directly above the ring to provide coaxial illumination such that the ring of light produced by the device is evenly illuminated. If incident light is received obliquely by the glass ring, much of the incident light will be blocked by the portion of the stainless steel rim nearest the light resulting in reduced light being emitted from that side of the glass ring. On the side of the glass furthest from the light, the stainless steel rim does not block the light and actually reflects additional light into the glass ring such that the circle of light directed to the eye is uneven creating difficulty in determining the extent of any reflected oval. Additionally, frosted areas of the glass ring where it is cut on the inside and the outside, causes reflection of a circle of light appearing to be a double ring furthest from the light and a single ring nearest the light with oblique illumination. This device, accordingly, has the disadvantage of being useless, from a practical standpoint, when obliquely illuminated, it being noted that surgical loupes and many operating microscopes are obliquely illuminated.

SUMMARY OF THE INVENTION

Accordingly, it is a primary object of the present invention to overcome the above mentioned disadvantages of prior art keratometers by providing a hand-held keratometer useful with coaxial and oblique light sources.

Another object of the present invention is to construct a sterilizable, hand-held, non-ocular contact keratometer useful with all surgical loupes and microscopes in the control of corneal astigmatism.

A further object of the present invention is to construct a keratometer of a plastic ring having a roughened surface such that the ring will catch all possible incident light and project a true circle onto the cornea of the eye.

The present invention has an additional object in that a keratometer is constructed of a ring of plastic material having a rectangular configuration in cross section to produce a precisely defined circle of light.

Yet another object of the present invention is to provide indicia on a hand-held keratometer to facilitate determination of the axis and extent of astigmatism.

Some of the advantages of the present invention over the prior art are that the keratometer of the present invention can be hand-held and easily manipulated by a surgeon for use with various types of surgical loupes and microscopes, can be used with both coaxial and oblique light sources to produce a precisely defined circle of light of even illumination, facilitates location of the axis and extent of astigmatism to simplify correction, and can be simply and inexpensively manufactured while being sterilizable or autoclavable.

The present invention is generally characterized in a keratometer comprising an elongate handle, and a circular ring of transparent material mounted on the handle and having a roughened surface to collect incident light and project a circle of light for use in measuring astigmatism of the eye.

Other objects and advantages of the present invention will become apparent from the following description of the preferred embodiment taken in conjunction with the accompanying drawings.

BRIEF DESCRIPTION OF THE DRAWINGS

FIG. 1 is a plan view of a keratometer according to the present invention.

FIG. 2 is a side elevation of the keratometer of the present invention.

FIG. 3 is a section taken along line 3—3 of FIG. 1.

FIG. 4 is a perspective view illustrating the use of the keratometer of the present invention to project a circle of light toward an eye.

FIG. 5 is an illustration of a circle of light projected by the keratometer of the present invention and the oval reflection of an astigmatic eye.

DESCRIPTION OF THE PREFERRED EMBODIMENT

A keratometer 10 according to the present invention is illustrated in FIG. 1 and is composed of a handle 12 having a neck 14 of reduced dimensions and a ring 16 mounted on the handle 12 at neck 14 and formed of a perfect circle of light transparent material. The ring 16 is rectangular in cross-sectional configuration with sharp right angle corners forming inner and outer edges 18 and 20 of the ring, respectively, and the ring has a surface 22 roughened to catch incident light. The roughened surface can be formed in any suitable manner, such as by physically scratching the surface or otherwise causing the surface to be erose, or the roughened texture of the surface can be formed when molding the ring.

The handle 12 has a free end 24 preferably having a width greater than the width of neck 14 at which the ring is mounted. It is important that the width of the neck be as small as possible so as to provide an abrupt or sharp junction between the handle and ring and thereby cause the ring to stand out and be clearly distinct from the handle. To this end, it is additionally desirable that the neck 14 have a thickness less than the thickness of the ring 16, as shown in FIG. 2, to prevent the neck of the handle from blending with the ring.

By mounting the ring to be distinct from the handle, the circle of light produced by the ring for projection on an eye is well defined, and the projected circle of light is further defined by the inner edge 18 and the outer edge 20 of surface 22 having sharp, right angled configurations.

To facilitate determination by a surgeon of the radial location of the long axis of an oval reflected by an astigmatic eye, degree indicia 26 are radially arranged on the roughened surface 22 of the ring such that the surgeon can align the axis of the reflected oval with the scale indicia. Additionally, shape indicia 28 are disposed on the handle 12 on the same side of the keratometer as the indicia 26 to permit simultaneous viewing by the surgeon, the shape indicia providing standard size ovals of reflected images from astigmatic eyes to permit comparison by the surgeon to determine the extent of astigmatism, i.e. the extent the eye is out of round. Preferably, the shape indicia will include ovals presenting one diopter, two diopters and three dipoters of astigmatism, it being appreciated that normally astigmatisms greater than three diopters must be corrected.

In use, the keratometer 10 will be held between an eye to be measured 30 and a source of light 32, as shown in FIG. 4, the light from the source being caught by the roughened surface 22 to project a perfect circle 34 of even illumination regardless of the angle of incidence of the light. The circle of light 34 will reflect a circle if the eye is perfectly round; however, if the eye is astigmatic, an oval will be reflected as shown at 36 in FIG. 5, the projected circle of light 34 also being illustrated in this figure. The surgeon can easily determine the radial location of the long axis of the oval 36 by reference to degree indicia 26, and the size of the oval, which corresponds to the extent of astigmatism, can be determined by comparison with the shape indicia 28.

Preferably, the keratometer is integrally formed of a transparent plastic material with the ring having a 12 mm inner diameter and a 14 mm outer diameter. The roughened surface 22 can be formed by scratching the material, for example with use of coarse sandpaper, or by any other suitable means.

Inasmuch as the present invention is subject to many variations, modifications and changes in detail, it is intended that all subject matter discussed above or shown in the accompanying drawings be interpreted as illustrative and not in a limiting sense.

What is claimed is:

1. A keratometer comprising:
   an elongate handle; and
   a circular ring of transparent material mounted on said handle and having a roughened surface to collect incident light and project a circle of light for use in measuring astigmatism of the eye;
   wherein said ring carries radially arranged indicia to locate the axis of astigmatism; and
   wherein said handle carries indicia shapes representative of standards of astigmatism to facilitate the determination of the extent of astigmatism present in an eye being measured by comparison.

2. A keratometer comprising:
   an elongate handle; and
   a circular ring of transparent material mounted on said handle and having a roughened surface to collect incident light and project a circle of light for use in measuring astigmatism of the eye;
   wherein said handle carries indicia shapes representative of standards of astigmatism to facilitate the determination of the extent of astigmatism present in an eye being measured by comparison.

3. A keratometer comprising:
   an elongate handle; and
   a circular ring of transparent material mounted on said handle and having a roughened surface to collect incident light and project a circle of light for use in measuring astigmatism of the eye;
   wherein said handle has a free end and a neck joining said ring having a width less than the width of said free end;
   wherein said ring is rectangular in cross section;

wherein said ring and said handle are integrally formed of plastic material; and wherein said roughened surface of said ring carries radially arranged indicia for locating the axis of astigmatism, and said handle carries shape indicia representative of standards of astigmatism for determining by comparison the extent of astigmatism present in an eye being measured, said radially arranged indicia and said shape indicia being disposed to be simultaneously visible.

* * * * *